(12) United States Patent
Rao et al.

(10) Patent No.: US 11,583,478 B2
(45) Date of Patent: Feb. 21, 2023

(54) RECONSTITUTABLE POWDER

(71) Applicant: Godrej Consumer Products Limited, Mumbai (IN)

(72) Inventors: Yadlapalli Venkateswara Rao, Mumbai (IN); Sandeep Arun Naik, Mumbai (IN); Harshad Premanand Pawar, Mumbai (IN)

(73) Assignee: Godrej Consumer Products Limited, Mumbai (IN)

( * ) Notice: Subject to any disclaimer, the term of this patent is extended or adjusted under 35 U.S.C. 154(b) by 0 days.

(21) Appl. No.: 16/992,763

(22) Filed: Aug. 13, 2020

(65) Prior Publication Data
US 2022/0047466 A1  Feb. 17, 2022

(51) Int. Cl.
*A61K 8/02* (2006.01)
*A61K 8/73* (2006.01)
*A61K 8/97* (2017.01)
*A61K 8/46* (2006.01)
*A61K 8/42* (2006.01)
*A61K 8/44* (2006.01)
*A61Q 5/02* (2006.01)
*A61Q 19/10* (2006.01)
*A61K 8/04* (2006.01)

(52) U.S. Cl.
CPC .............. *A61K 8/022* (2013.01); *A61K 8/042* (2013.01); *A61K 8/42* (2013.01); *A61K 8/44* (2013.01); *A61K 8/463* (2013.01); *A61K 8/731* (2013.01); *A61K 8/737* (2013.01); *A61K 8/97* (2013.01); *A61Q 5/02* (2013.01); *A61Q 19/10* (2013.01); A61K 2800/43 (2013.01); A61K 2800/48 (2013.01); *A61K 2800/51* (2013.01); *A61K 2800/524* (2013.01); *A61K 2800/596* (2013.01); *A61K 2800/87* (2013.01); *A61K 2800/882* (2013.01)

(58) Field of Classification Search
CPC .... A61K 8/022; A61K 8/97; A61K 2800/596; A61K 2800/882; A61Q 5/02; A61Q 19/10
See application file for complete search history.

(56) References Cited

U.S. PATENT DOCUMENTS

| 474,788 | A | 5/1892 | Webb |
| 9,150,818 | B2 | 10/2015 | Weller-Brophy et al. |
| 2005/0197263 | A1* | 9/2005 | Lambino ................ A61K 8/927 510/141 |
| 2016/0022566 | A1* | 1/2016 | Figura ................... A61K 8/898 510/125 |

OTHER PUBLICATIONS

AMP (https://www.ampfloracel.com/blog/benefits-of-aloe-vera-powder-for-hair-growth/), Jan. 19, 2020, pp. 1-7 (Year: 2020).*
Agarwal, A. (https://www.bebeautiful.in/all-things-skin/everyday/9-benefits-of-neem-leaves-for-skin-and-hair) Dec. 19, 2019, pp. 1-12 (Year: 2019).*
MacLeman, E. (https://thedermreview.com/disodium-edta/) Aug. 27, 2020, pp. 1-8 (Year: 2020).*

* cited by examiner

*Primary Examiner* — Andrew S Rosenthal
(74) *Attorney, Agent, or Firm* — Kramer & Amado, P.C.

(57) ABSTRACT

A reconstitutable surfactant-based powder has good solubility in water and forms a stable gel when dispersed in water. The reconstitutable surfactant-based powder consists of a polymer/gum system and a dry powder extract.

19 Claims, No Drawings

RECONSTITUTABLE POWDER

FIELD OF INVENTION

The invention is in the field of personal care products. More particularly, the current invention relates to a reconstitutable powder for personal care.

BACKGROUND OF THE INVENTION

Personal care or toiletries are consumer products used in personal hygiene and for beautification. Traditionally, most of these products are sold as liquid products. The major disadvantages with respect to liquid products are in terms of storage, packaging, the degree of preservation required, and convenience of use. Further, since liquid are mainly water based there is a chance of leakage arising out of improper handling during transportation or sudden bumping of the vehicle while trading a particularly uneven road. Further, Liquid cleansing products typically are sold in bottles. The cost of the bottle frequently contributes significantly to the overall cost of the product.

With a view of overcoming these drawbacks posed by liquid detergents, inventors have come up with a solution which constitutes usage of powder. However, usage of powder has its own set of disadvantages which may encompass soap residues left behind on your clothes, after washing. This leads to a need of follow-up wash (es).

Therefore, an ideal solution would be to devise a product which combines advantages of both powder and liquid, while simultaneously minimising the individual disadvantages posed by the powder and liquid products.

One solution for above problems is provided by EP1574203 (EP '203). Accordingly, the product as disclosed in EP '203 is a rehydratable personal care product which is converted to liquid as and when required. Since, the end-user product is a liquid product, the disadvantage of liquid as enumerated hereinbefore are not completely eliminated.

Therefore, the best solution would be to overcome all the disadvantages as listed above would be to devise a product which does not form a liquid after reconstitution. This could be achieved by forming a gel as an end-use product.

Hence, the current inventors have invented a novel product which is a solid while transportation and can be converted to a more usable gel formulation.

SUMMARY OF INVENTION

With a view of overcoming the above problems current inventors provide a solution which forms gel as an end-use product.

In an aspect, the invention is a reconstitutable surfactant-based powder product for personal care which has good solubility in water and forms a stable gel when dispersed in water.

In various embodiments disclosed herein, the reconstitutable surfactant based powder having good solubility in water and forming a stable gel when dispersed in water, and contains 12 to 22% by weight a polymer/gum system; 0.001 to 10% by weight one or more dry powder extracts; 5-95% by weight surfactants and co-surfactants; 2-30% by weight one or more thickening and stabilizing agents; 0.3 to 2% by weight one or more chelating agents; 0.4 to 3% by weight one or more preservatives; and 0-5% by weight of water. The dry powder extract powder may be at least one natural extract coated over silica. The natural extract coated over silica may be Aloe Vera, Neem, or a combination thereof.

The reconstitutable powder may also include at least one of a buffering agent, a conditioning agent, an herbal extract, a fragrance, a coloring agent, and an anticaking agent.

In various embodiments, the reconstitutable powder may be used in a personal care product, such as a shampoo, a body wash, or a hand wash. In some embodiments, the reconstitutable powder may be used in a household cleaning product.

In various embodiments disclosed herein, the reconstitutable powder contains a polymer/gum system including a material selected from the group consisting of cellulose, guar gum, xanthan gum, trimethyl cellulose (TMC), Hydroxypropyl methylcellulose (HPMC), Carboxymethyl Cellulose (CMC), or a combination thereof. The polymer/gum system may include at least two materials selected from the group consisting of cellulose, guar gum, xanthan gum, trimethyl cellulose (TMC), Hydroxypropyl methylcellulose (HPMC), and Carboxymethyl Cellulose (CMC).

In various embodiments disclosed herein, the reconstitutable powder contains a polymer selected from the group consisting of cellulose, trimethyl cellulose (TMC), Hydroxypropyl methylcellulose (HPMC), Carboxymethyl Cellulose (CMC), and mixtures thereof, and a gum which is different from the polymer, selected from the group consisting of guar gum, xanthan gum, Hydroxypropyl methylcellulose (HPMC), and Carboxymethyl Cellulose (CMC), where a ratio of polymer to gum is between 1:5 and 1:10, between 1:6 and 1:8, or about 1:7.5.

The reconstitutable powder may include a polymer selected from the group consisting of cellulose, trimethyl cellulose (TMC), Hydroxypropyl methylcellulose (HPMC), Carboxymethyl Cellulose (CMC), and mixtures thereof; and a gum selected from the group consisting of guar gum and xanthan gum; where a ratio of polymer to gum is between 1:5 and 1:10, between 1:6 and 1:8, or about 1:7.5.

The reconstitutable powder may include a polymer/gum system including:

from 1% to 5% by weight, from 1.5% to 3% by weight, or from 2% to 2.5% by weight of the powder of a polymer selected from the group consisting of cellulose, trimethyl cellulose (TMC), Hydroxypropyl methylcellulose (HPMC), Carboxymethyl Cellulose (CMC), and mixtures thereof, and from 10% to 25% by weight, from 12% to 18% by weight, or from 14% to 16% by weight of the powder of a gum which is different from the polymer, selected from the group consisting of guar gum, xanthan gum, Hydroxypropyl methylcellulose (HPMC), and Carboxymethyl Cellulose (CMC).

In various embodiments disclosed herein, the reconstitutable surfactant-based powder contains:

12 to 22% by weight of the polymer/gum system;

0.001 to 10% by weight of one or more dry powder extracts;

5-95% by weight surfactants and co-surfactants, where the surfactants or co-surfactants may be anionic and/or amphoteric surfactants;

2-30% by weight one or more thickening and stabilizing agents;

0.3 to 2% by weight one or more chelating agents;

0.4 to 3% by weight one or more preservatives; and 0-5% by weight of water. The chelating agent may be Ethylenediaminetetraacetic acid (EDTA), Disodium Ethylenediaminetetraacetic acid (Na2-EDTA), Nitrilotriacetic acid (NTA), or a combination thereof. The anionic surfactant may be Disodium Lauryl Sulfosuccinate, Sodium lauryl Sulphate, or a combination thereof. The amphoteric surfactant may be cocamidopropyl betaine, which may be used alone or in combination with an anionic surfactant.

Various embodiments disclosed herein relate to a sachet comprising a reconstitutable surfactant-based powder containing:
- 12 to 22% by weight of the polymer/gum system;
- 0.001 to 10% by weight of one or more dry powder extracts;
- 5-95% by weight surfactants and co-surfactants, where the surfactants or co-surfactants may be anionic and/or amphoteric surfactants;
- 2-30% by weight one or more thickening and stabilizing agents;
- 0.3 to 2% by weight one or more chelating agents;
- 0.4 to 3% by weight one or more preservatives; and
- 0-5% by weight of water.

In various embodiments, the reconstitutable surfactant-based powder may be reconstituted to form a gel by:
- filling an empty pump bottle with water;
- emptying a sachet containing the reconstitutable surfactant-based powder into the water-filled pump bottle;
- shaking the water-filled pump bottle to disperse the reconstitutable surfactant-based powder, and
- allowing the bottle to stand until a stable gel is formed.

A kit for cleansing includes a sachet containing the reconstitutable surfactant-based powder, and a container, e.g., a pump bottle, for reconstituting the reconstitutable powder and dispensing a reconstituted gel.

DETAILED DESCRIPTION OF THE INVENTION

Described herein is a reconstitutable surfactant-based powder product which has good solubility in water and forms a stable gel when dispersed in water.

The reconstitutable surfactant-based powder of the invention is a dry mixture of surfactants that provide cleansing. Said Reconstitutable powder consists of a polymer/gum system conferring gelling and stability to the formulation upon reconstitution. The reconstitutable surfactant-based powder may also contain effective amounts of stabilizers and buffers, appropriate natural or artificial conditioning agents, natural ingredients like Aloe Vera and Neem, fragrances, and colours.

In an embodiment, the reconstitutable powder of the invention comprise of a 12-22% polymer/gum system conferring gelling and stability to the formulation upon reconstitution, 0.001 to 10% by weight one or more dry powder extracts, 5-95% by weight surfactants and co-surfactants, 2-30% by weight one or more thickening and stabilizing agents, 0-5% by weight of water. The powder formulation further comprises 0.3 to 2% by weight chelating agent, buffering agents and 0.4 to 3% by weight preservatives. Preferably, dry powder extracts of Aloe Vera and Neem are coated/adsorbed on Silica to provide the reconstitutable powder of the invention with 0.2 to 1.0% by weight fragrance and impart conditioning and germ washing property the formulation. In an Optional embodiment, the powder formulation may further comprise, conditioning agents, herbal extracts, fragrance, colour, and anticaking agents.

In accordance with above embodiment, the polymer/gum system may be selected from, but not limited to, Cellulose, Gaur Gum, xanthan gum, trimethyl cellulose (TMC), Hydroxypropyl methylcellulose (HPMC), Carboxymethyl Cellulose (CMC), or combinations thereof.

In accordance with above embodiment, the chelating agent could be selected from EDTA, Disodium EDTA, Nitrilotriacetic acid, or combinations thereof.

The powder formulation can be used directly or with water preferably after reconstitution, to prepare cleansing products such as shampoo, body wash, hand wash and household cleaning products.

In an embodiment, the powder sachet is provided with an empty pump bottle. The empty bottle is filled with water up to a recommended level, into which the sachet is to be emptied. The, hence, filled bottle is shaken for 2-3 min to disperse the powder well. It takes approximately two (2) hours to get a good gel that can be easily pumped out of bottle. Accordingly, the 9 gms to 10 gms of the reconstitutable powder of the invention is mixed in 200 ml water.

In an embodiment, the invention provides a kit for cleansing. The kit contains a sachet containing the reconstitutable powder and container for reconstituting the reconstitutable powder and dispensing reconstituted gel. Preferably, the container for reconstituting the reconstitutable powder and dispensing reconstituted gel is a pump bottle made up of a transparent material. Said container could be demarcated to indicate specific volume, preferably 200 ml.

EXAMPLE

Several examples are set forth below to further illustrate the nature of the invention and the manner of carrying it out. However, the invention should not be considered as being limited to the details thereof.

Example 1

| Sr. No. | INCI Name | Range % |
|---|---|---|
| 1 | Silicon Dioxide | 0.2 to 3.0 |
| 2 | Fragrance | 0.2 to 1.0 |
| 3 | Polymer/Gum (Cellulose & Gaur Gum) | 12 to 22 |
| 5 | Chelating agent | 0.3 to 2 |
| 6 | Preservative | 0.4 to 3 |
| 7 | Colour | 00.020 to 0.008 |
| 8 | Aloe Vera Extract | 00.001-0.005 |
| 9 | Neem Extract | 00.001-0.005 |
| 10 | Anionic Surfactant (Disodium Lauryl Sulfosuccinate & Sodium lauryl Sulphate) | 5-90.0 |
| | Total | 100.000 |

Process for reconstitution of powder:
a. Filling an empty pump bottle with 200 ml of water;
b. empting the sachet containing 9 gm to 10 gm of reconstitutable powder to the filled pump bottle of step (a);
c. shaking the filled pump bottle of step (b) for dispersing the powder, and
d. Allowing the bottle to stand to get good gel for about 2 hours.

We claim:
1. A reconstitutable surfactant-based powder, wherein the reconstitutable powder is water-soluble and forms a stable gel when dispersed in water, comprising:
a. 12 to 22% by weight of a polymer/gum system;
b. 0.001 to 10% by weight of a dry powder extract, wherein the dry powder extract comprises at least one natural extract adsorbed onto silica;
c. 5-95% by weight of surfactants and co-surfactants;
d. 2-30% by weight of one or more thickening and stabilizing agents;

e. 0.3 to 2% by weight of one or more chelating agents;
f. 0.4 to 3% by weight of one or more preservatives;
g. 0-5% by weight of water.

2. The reconstitutable powder as claimed in claim 1, wherein the natural extract adsorbed onto silica is selected from the group consisting of Aloe Vera, Neem, and combinations thereof.

3. The reconstitutable powder as claimed in claim 1, further comprising at least one of:
   a buffering agent,
   a conditioning agent,
   an herbal extract,
   a fragrance,
   a coloring agent, and
   an anticaking agent.

4. The reconstitutable powder as claimed in claim 1, wherein the reconstitutable powder is used in a shampoo, a body wash, a hand wash, or a household cleaning product.

5. The reconstitutable powder as claimed in claim 4, wherein the reconstitutable powder is used in a hand wash.

6. The reconstitutable powder as claimed in claim 1, wherein the polymer/gum system comprises a material selected from the group consisting of cellulose, guar gum, xanthan gum, trimethyl cellulose (TMC), Hydroxypropyl methylcellulose (HPMC), Carboxymethyl Cellulose (CMC), and a combination thereof.

7. The reconstitutable powder as claimed in claim 1, wherein the polymer/gum system comprises at least two materials selected from the group consisting of cellulose, guar gum, xanthan gum, trimethyl cellulose (TMC), Hydroxypropyl methylcellulose (HPMC), and Carboxymethyl Cellulose (CMC).

8. The reconstitutable powder as claimed in claim 1, wherein the polymer/gum system comprises:
   a polymer selected from the group consisting of cellulose, trimethyl cellulose (TMC), Hydroxypropyl methylcellulose (HPMC), Carboxymethyl Cellulose (CMC), and mixtures thereof, and
   a gum which is different from the polymer, selected from the group consisting of guar gum, xanthan gum, Hydroxypropyl methylcellulose (HPMC), and Carboxymethyl Cellulose (CMC),
   wherein a ratio of polymer to gum is between 1:5 and 1:10.

9. The reconstitutable powder as claimed in claim 1, wherein the polymer/gum system comprises a polymer selected from the group consisting of cellulose, trimethyl cellulose (TMC), Hydroxypropyl methylcellulose (HPMC), Carboxymethyl Cellulose (CMC), and mixtures thereof; and a gum selected from the group consisting of guar gum and xanthan gum; wherein a ratio of polymer to gum is between 1:6 and 1:8.

10. The reconstitutable powder as claimed in claim 1, wherein the polymer/gum system comprises:
    from 1% to 5% by weight of the powder of a polymer selected from the group consisting of cellulose, trimethyl cellulose (TMC), Hydroxypropyl methylcellulose (HPMC), Carboxymethyl Cellulose (CMC), and mixtures thereof, and
    from 10% to 25% by weight of the powder of a gum which is different from the polymer, selected from the group consisting of guar gum, xanthan gum, Hydroxypropyl methylcellulose (HPMC), and Carboxymethyl Cellulose (CMC).

11. The reconstitutable powder as claimed in claim 1, wherein the polymer/gum system comprises:
    from 1.5% to 3% by weight of the powder of a polymer selected from the group consisting of cellulose, trimethyl cellulose (TMC), Hydroxypropyl methylcellulose (HPMC), Carboxymethyl Cellulose (CMC), and mixtures thereof; and
    from 12% to 18% by weight of the powder of a gum selected from the group consisting of guar gum and xanthan gum.

12. The reconstitutable powder as claimed in claim 1, wherein the chelating agent is selected from the group consisting of Ethylenediaminetetraacetic acid (EDTA), Disodium Ethylenediaminetetraacetic acid (Nar-EDTA), Nitrilotriacetic acid (NTA), or a combination thereof.

13. The reconstitutable powder as claimed in claim 1, wherein the surfactant comprises an Anionic Surfactant selected from the group consisting of Disodium Lauryl Sulfosuccinate, Sodium lauryl Sulphate, and combinations thereof.

14. The reconstitutable powder as claimed in claim 1, wherein the surfactant comprises cocamidopropyl betaine.

15. The reconstitutable powder as claimed in claim 13, wherein the surfactant further comprises cocamidopropyl betaine.

16. A sachet comprising the reconstitutable surfactant-based powder of claim 1.

17. A method for reconstituting the reconstitutable surfactant-based powder of claim 1, comprising:
    a. filling an empty pump bottle with water;
    b. emptying a sachet containing the reconstitutable surfactant-based powder into the filled pump bottle of step (a);
    c. shaking the filled pump bottle of step (b) to disperse the reconstitutable surfactant-based powder, and
    d. allowing the bottle to stand until a stable gel is formed.

18. A kit for cleansing comprising:
    a) a sachet containing the reconstitutable surfactant-based powder of claim 1, and
    b) a container for reconstituting the reconstitutable powder and dispensing a reconstituted gel.

19. The kit as claimed in claim 18, wherein the container is a pump bottle.

* * * * *